United States Patent [19]

Alps et al.

[11] Patent Number: 5,733,871
[45] Date of Patent: Mar. 31, 1998

[54] METHODS FOR THE TREATMENT OF NEURONAL DAMAGE ASSOCIATED WITH ISCHEMIA, HYPOXIA OR NEURODEGENERATION

[75] Inventors: Brian J. Alps, Linlithgow; Christine Mary Brown, Glasgow, both of Scotland; Franklin D. Collins, Agoura Hills; Caroline J. Emmett, Belmont, both of Calif.; Michael Spedding, Le Vesinet, France; Deborah Russell, Boulder, Colo.; Seth P. Finklestein, Needham; Michael A. Moskowitz, Belmont, both of Mass.; Roger Lewis Whiting, Los Altos, Calif.

[73] Assignee: The General Hospital Corporation, Boston, Mass.

[21] Appl. No.: 30,429

[22] PCT Filed: Nov. 6, 1992

[86] PCT No.: PCT/US92/09618

§ 371 Date: Mar. 16, 1995

§ 102(e) Date: Mar. 16, 1995

[87] PCT Pub. No.: WO93/08828

PCT Pub. Date: May 13, 1993

Related U.S. Application Data

[63] Continuation-in-part of Ser. No. 790,734, Nov. 8, 1991, abandoned.

[51] Int. Cl.[6] .................. A61K 38/00; A61K 38/27; A61K 38/16; A61K 38/28

[52] U.S. Cl. .................. 514/12; 514/21; 530/399
[58] Field of Search .................. 514/12, 21; 530/399

[56] References Cited

U.S. PATENT DOCUMENTS

| | | | |
|---|---|---|---|
| 4,296,100 | 10/1981 | Franco | 514/21 |
| 4,994,559 | 2/1991 | Moscatelli | 530/399 |
| 5,011,914 | 4/1991 | Collins | 530/399 |
| 5,057,494 | 10/1991 | Sleffield | 514/12 |

FOREIGN PATENT DOCUMENTS 930882  6/1993  WIPO.

OTHER PUBLICATIONS

R. Morrison et al. PNAS, 83, 7532–7541, 1986.
Walicke et al., Experimental Neurology, 102, 144–48, 1988.
FisCher et al. Nature: vol. 329(3) pp. 65–68, (1987).
Remington's Pharmaceutical Science, 16 pp. 759–760.

*Primary Examiner*—Cecilia J. Tsang
*Assistant Examiner*—P. L. Touzeau
*Attorney, Agent, or Firm*—Fish & Richardson P.C.

[57] ABSTRACT

Intravenous administration and pharmaceutically acceptable compositions of neurotrophic factors for treating neuronal damage in the central nervous system of individuals in need of such treatment are disclosed. The neuronal damage associated with ischemia, hypoxia, or neurodegeneration may result from stroke or cardiac arrest. This invention provides for the intravenous administration of neurotrophic factors such as bFGF, aFGF, NGF, CNTF, BDNF, NT3, NT4, IGF-I and IGF-II.

4 Claims, 5 Drawing Sheets

METHODS FOR THE TREATMENT OF NEURONAL DAMAGE ASSOCIATED WITH ISCHEMIA, HYPOXIA OR NEURODEGENERATION

This application is a 371 of PCT/US 92/09618, filed Nov. 6, 1992, which is a continuation-in-part of U.S. application Ser. No. 07/790,734, filed Nov. 8, 1991, now abandoned entitled "Intravenous Methods and Pharmaceutical Composition of Neurotrophic Factors For Treatment of Neuronal Damage Associated with Ischemia, Hypoxia or Neurodegeneration", pending.

TECHNICAL FIELD OF THE INVENTION

This invention relates to pharmaceutical compositions useful for treatment of neuronal damage associated with ischemia, hypoxia or neurodegeneration, and to methods for using the compositions.

BACKGROUND OF THE INVENTION

Neurotrophic factors exhibit a trophic effect on neuronal cells of the brain. The trophic effect has been characterized as enhancing neuronal survival and maintenance of neuronal cell functions associated with differentiated neurons. In vivo studies have shown that a variety of endogenous and exogenous neurotrophic factors exhibit a trophic effect on neuronal cells after ischemic, hypoxic or other disease-induced damage. Examples of specific neurotrophic factors include basic fibroblast growth factor (bFGF), acidic fibroblast growth factor (aFGF), nerve growth factor (NGF), ciliary neurotrophic factor (CNTF), brain derived neurotrophic factor (BDNF), neurotrophin 3 (NT3), neurotrophin 4 (NT4) and the insulin-like growth factors I and II (IGF-I, IGF-II).

Some neurotrophic factors, such as bFGF and CNTF, are thought to have broad trophic effects, promoting survival or providing a maintenance function for many different types of neuronal cells. Other neurotrophic factors have a narrower, more specific trophic effect and promote survival of fewer types of cells. For example, in the peripheral nervous system NGF promotes neuronal survival and axonal extension of certain specific neuronal cell types such as sensory and sympathetic neurons (Ebendal, T. et al., *Cellular and Molecular Biology of Neuronal Development*, Ch. 15, ed. Black, I. B., 1984). However, in the CNS, NGF also supports the survival of cholinergic neurons in the basal forebrain complex (Whittemore et al., *Brain Res. Rev.*, 12:439–464, 1987). BDNF, a basic protein of molecular weight 12,300, supports some sensory neurons that do not respond to NGF (Barde, et al., *EMBO J.*, 1:549–553, 1982 and Hofer and Barde, *Nature*, 331:261–262, 1988). Neurotrophin 3 (NT3) supports survival of dorsal root ganglion neurons and proprioceptive neurons in the trigeminal mesencephalic nucleus. CNTF, a protein of about molecular weight 23,000, supports ciliary ganglion neurons in the parasympathetic nervous system, sympathetic neurons, dorsal root ganglion neurons in the sensory nervous system and motor neurons in the central nervous system (CNS) (Kandel, E. R., et al., *Principles of Neural Science*, 3rd Ed., Elsevier Science Publishing Co., Inc., New York, 1991).

Some neurotrophic factors constitute a family of neurotrophic factors characterized by about 50% amino acid homology. One such family is the BDNF/NGF family, which includes BDNF, NGF, NT3 and NT4 (Hohn, A., et al., WO 91/03569).

Fibroblast growth factors (FGFs) are members of a protein family that induce mitogenic, chemotactic and angiogenic activity in a variety of cells of epithelial, mesenchymal, and neuronal origins (Zhu et al., 1990; Moscatelli, et al., U.S. Pat. No. 4,994,559). FGFs are proteins of molecular weight 16,000–25,000 and characterized by their strong binding to heparin (Finklestein, S., et al., Stroke (Suppl. III) III-122–III-124, 1990; Finklestein, S. et al., *Rest. Neurol. and Neurosci.*, 1:387–394, 1990). Both aFGF and bFGF have been reported to have broad specificity of neurotrophic activities. Although the FGFs have similar functional activities, they are discretely different proteins with different properties.

Because of the ability of neurotrophic factors to promote the survival of neurons, they have been suggested to be useful for treating various disorders associated with neuronal cell death. Intracisternal administration of bFGF to rats after middle cerebral artery occlusion was reported to prevent thalamic degeneration (Yamada, K., et al., *J. Cerebral Blood Flow and Met.*, 11:472–478, 1991). Continuous intracerebroventricular infusion of aFGF to a gerbil prevented death of hippocampal CA1 pyramidal cells after 5 minute ischemia (Oomora, Y., et al., *Soc. for Neurosci. Abstracts*, 16(1):516 Abstr. No. 221.2, 1990).

Administration of neurotrophic factors in the periphery for a site of action in the CNS presents several problems. For example, in vivo intravenous administration of neurotrophic factors subjects them to degradative processes in the body, including proteases, which can breakdown the protein prior to its desired action in the CNS. Many charged molecules, including neurotrophic factors, bind to the extracellular matrix. Some neurotrophic factors affect non-neuronal cells, e.g., FGFs. Such activity may decrease the neurotrophic factor's ability to act on neuronal cells. In addition, the administration of drugs into the periphery for uptake into the CNS presents unique challenges because the blood-brain barrier prevents the entry of large molecules into the cerebral extracellular space and cerebral spinal fluid (CSF).

CSF, found within the brain ventricles and surrounding the brain and spinal cord, is extracellular fluid that bathes neurons and glial cells in the central nervous system. The blood-brain barrier separates the blood from direct contact with brain cells and CSF. In general, only small lipophilic solutes are able to diffuse freely between the blood vessels and the CSF. Large hydrophilic molecules, proteins and the like, generally are incapable of diffusion through the blood-brain barrier but some are actively transported across. Generally, strongly ionized and/or lipid insoluble drugs are excluded from the brain. Non-ionized forms of weak acids and bases are somewhat restricted, but their entry increases in proportion to their lipid solubility. However, highly lipid soluble drugs enter the brain rapidly (*Goodman and Gilman's The Pharmacological Basis of Therapeutics*, 6th Eds., Eds. Goodman, L. S. and Gilman, A., Macmillan Publishing Co., Inc. (1980) pp. 10, 244).

Intravenous administration of small molecules for experimental treatment of neuronal damage associated with CNS ischemia has been done. For example, Kofke, W. A., et al., *Stroke*, 10(5):554–560 (1979) report that the barbiturate thiopental when administered intravenously (IV) to rhesus monkeys following global brain ischemia produced by trimethaphan-induced hypotension and a high pressure neck tourniquet, improved distribution of brain blood flow and glucose uptake.

To overcome the difficulties presented by the blood-brain barrier, molecules thought to be either too large or lipid-insoluble are generally administered into the CNS by direct intraventricular injections or by way of drug impregnated implants (Otto, D., et al., *J. Neurosci. Res.*, 22:83–91 (1989); Goodman & Gilman's *The Pharmacological Basis of Therapeutics*, 6th Ed. at 244). Another administration route is by continuous infusion through an intracerebroventricular cannula device (Williams, L. R., et al., *Proc. Natl. Acad. Sci. USA*, 83:9231–9235, 1986). For the above reasons, neurotrophic factors have been administered experimentally by direct injection into the brain, by impregnated gelfoam implants in the brain or by continuous infusion from an implanted pump into the cerebral ventricles of laboratory animals with induced ischemic or hypoxic damage. For example, Ortiz, A., et al., *Soc. Neurosci. Abstracts*, 386.18 (1990), reported that intraventricular injection of NGF could ameliorate behavioral dysfunction associated with ischemia due to middle cerebral artery and common carotid artery occlusion.

Even though intracerebroventricular administration avoids the problems presented by the blood-brain barrier and degradative processes associated with an intravenous route, e.g., proteases, this route is not preferred for routine administration to patients because it is invasive, difficult to implement and is associated with relatively high degree of risk compared to intravenous administration.

Chemical modification of neurotrophic factors is another approach to increasing neurotrophic factor permeability through the blood-brain barrier. Lewis, M. E., et al., WO 90/14838, suggest modifying IGF-I, IGF-II or NGF to increase lipophilicity, alter glycosylation or increase the net positive charge as a means of increasing the blood-brain barrier permeability of the neurotrophic factor.

Although some brain neurons die irrevocably soon after severe cerebral ischemia, others appear to undergo a "delayed neuronal death", occurring during the hours or days after ischemia. It is for these reasons that it is believed that there is an opportunity for therapeutic intervention following stroke. The "delayed neuronal death" phenomenon appears particularly true for certain "selectively vulnerable" neurons following global cerebral ischemia, and neurons at the borders or penumbra of infarcts following focal cerebral ischemia. Potential mechanisms of delayed neuronal death include excitatory amino acid (EAA) toxicity, free radical formation, and activation of intracellular "suicide" programs. In particular, extracellular EAA concentrations are elevated after transient ischemia, leading (through activation of the NMDA receptor) to massive $Ca^{2+}$ influx, and to subsequent initiation of lethal intracellular processes, including activation of proteases and endonucleases. Pharmacological blockade of NMDA receptor sites reduces neuronal damage in several models of focal cerebral ischemia.

SUMMARY OF THE INVENTION

The present invention provides a pharmaceutical composition for intravenous administration comprising a neurotrophic factor in an aqueous, pharmaceutically acceptable solution.

The present invention provides a method for treating or preventing neuronal damage in the central nervous system, which method comprises intravenous administration to a mammal in need thereof of a pharmaceutical composition comprising a therapeutically effective amount of a neurotrophic factor and a pharmaceutically acceptable carrier.

This invention also provides a method for treating or preventing neuronal damage in the central nervous system comprising administering intravenously a pharmaceutical composition comprising basic fibroblast growth factor (bFGF) and a pharmaceutically acceptable stabilizer that promotes the stability of bFGF.

More specifically, the present invention provides a method for treating global or focal cerebral ischemia with bFGF administered subsequent to the onset of ischemia. bFGF may be administered intracerebrally or intravenously up to 6 hours post ischemia.

DETAILED DESCRIPTION OF PREFERRED EMBODIMENTS

Figure 1A:
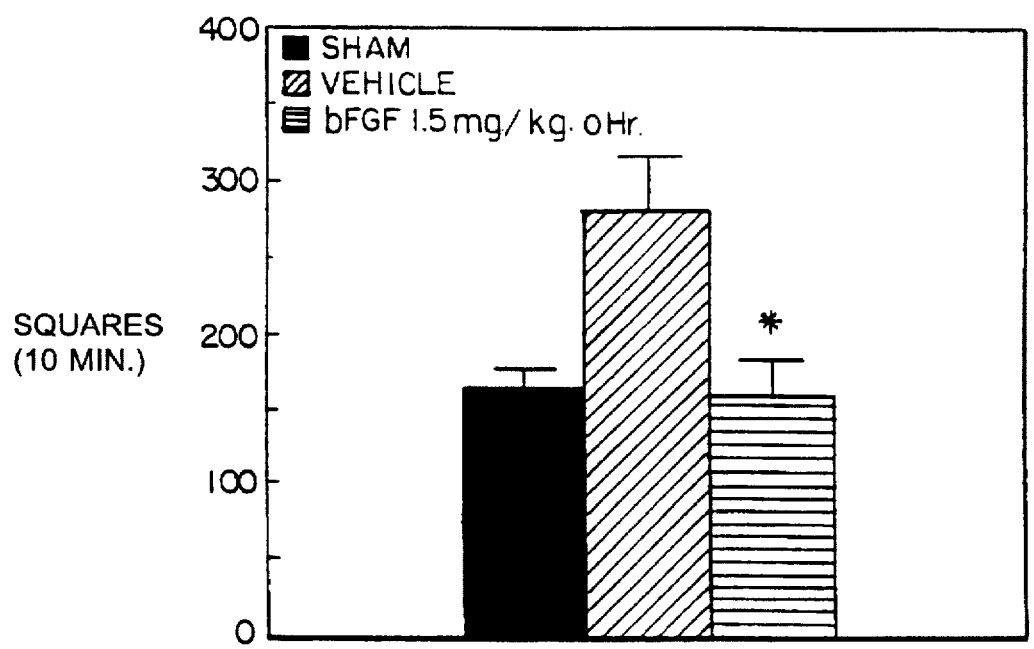
FIG. 1(*a–b*) depicts the effects of three bolus intravenous administrations of bFGF (1.5 mg/kg/injection at 0, 24, and 48 hr. post ischemia) on activity in an open field chamber and on the number of surviving hippocampal neurons. * indicates a significant difference between vehicle-treated and bFGF-treated by the unpaired t test (p<0.05). n=10 (sham), n=20 (vehicle treated), n=20 (bFGF-treated).

This invention relates to intravenous administration of neurotrophic factors to treat or prevent neuronal damage resulting from ischemia, hypoxia or neurodegeneration and pharmaceutical compositions for intravenous administration comprising a neurotrophic factor. It is surprising that the neurotrophic factors reach the CNS and are still active in the CNS following intravenous administration. Such methods and compositions are suitable for the treatment of stroke or cardiac arrest which result in ischemic or hypoxic damage or neurodegeneration and prophylactic use.

In alternate embodiments of the invention, the administration of neurotrophic factor may be accomplished by introducing the neurotrophic factor intracerebrally or intraventricularly. In this manner, issues relating to the blood/brain barrier are not relevant. However, in the preferred embodiment the neurotrophic factors are administered intravenously.

A neurotrophic factor is defined as any protein factor which promotes the survival of neurons. Some neurotrophic factors are also capable of promoting neurite outgrowth and glial cell and blood vessel restoration or inducing cells to secrete other neurotrophic factors. The neurotrophic factors are useful for treating neuronal damage caused by strokes and other neurological disorders associated with generalized cell hypoxia, ischemia or neurodegeneration. Preferred neurotrophic factors are those to which a broad range of cell types respond. More preferred neurotrophic factors may be selected from the group consisting of bFGF, aFGF, CNTF, NGF, BDNF, NT3, IGF-I and IGF-II and other members of the BDNF/NGF family. Particularly preferred neurotrophic factors included bFGF, CNTF and NGF. Most preferred is bFGF.

Neurotrophic factors may be obtained from a variety of sources, preferably mammalian, most preferably human and may be isolated from tissue or may be produced using recombinant technology. Recombinantly produced neurotrophic factors are preferred, and most preferred are human recombinantly produced neurotrophic factors. Neurotrophic factors include modified fragments of the native neurotrophic factors retaining neurotrophic activity. Neurotrophic factors also include modified forms of naturally existing neurotrophic factors retaining neurotrophic activity. Active fragments of neurotrophic factors may be identified by bioassays or receptor assays. Methods for obtaining various neurotrophic factors are known in the art, e.g., Moscatelli, et al., U.S. Patent 4,994,559 (bFGF), Collins, et al., U.S. Pat. No. 5,011,914 (CNTF), Chan, et al., EPO 370, 171 (NGF). The pharmaceutical composition may contain one or more neurotrophic factors. The choice of neurotrophic factors or a mixture will be guided by the type of neuronal cells intended to be treated. The neurotrophic factors of the prevent invention may also be chemically modified according to procedures known in the art in order to enhance penetration of the blood-brain barrier.

The amount of neurotrophic factor present in the pharmaceutical composition is an amount that is therapeutically effective, i.e., an amount which results in the improvement of neuronal function of neurons damaged by ischemia, hypoxia or neurodegeneration or prevents further neuronal damage. The total amount of neurotrophic factor in a dose will depend on the specific activity of the neurotrophic factor, severity of the damage, responsiveness of the patient and other factors. Methods to determine efficacy and dosage amount are known to those skilled in the art. The method of the invention provides a neurotrophic factor in a dose of about 0.1 µg/kg body weight to 100 mg/kg, preferably about 1.0 µg/kg to 50 mg/kg, more preferably about 10 µg/kg to 15 mg/kg and most preferably at least 0.2 mg/kg. The preferred total amount of bFGF when administration is intravenous is about 0.2 mg/kg to 10 mg/kg. A more preferred amount of total bFGF is about 1.5 mg/kg to 4mg/kg. The preferred total amount of bFGF when administered intracerebrally is 0.1 mg/kg to 10 µg/kg. A preferred total amount of NGF is about 1 mg/kg to 50 mg/kg. A more preferred total amount of NGF is about 14 mg/kg. A preferred total amount of CNTF is about 1 µg to 100 µg.

The timing of the initiation of the administration of the neurotrophic factor as described herein is an important factor in effectiveness. In the preferred embodiment, administration is begun as soon as possible following the onset of ischemia. However, the inventors have surprisingly found that the treatment may be effective even when treatment is initiated as much as 6 hours post-ischemia.

In certain situations, for example in patients undergoing cardiac surgery or who are on a heart lung machine, the neurotrophic factors of the present invention may be administered prophylactically. A small but significant percentage of those patients suffer brain ischemia during the procedure.

The neurotrophic factor of the present invention may be administered in the form of a pharmaceutical composition, wherein the neurotrophic factor is mixed with a pharmaceutically acceptable carrier. The nature of the carrier will vary depending on the nature of administration. Those skilled in the art are familiar with appropriate carriers for each of the commonly utilized methods of administration.

The pharmaceutical composition may be an aqueous solution which may contain pharmaceutical excipients standard for preparing intravenous injectable or infusible compositions. The composition may contain a buffer sufficient to adjust pH of the composition to 5.0–8.0. The physical nature of bFGF specifically requires that the protein be stabilized prior to administration in order for the bFGF to be biologically active as introduced into the patient. bFGF loses its activity rapidly in an aqueous solution, and generally must be formulated with a stabilization additive to prevent this deactivation. (See, European Patent Application 89110016.6; published as 0 345 660 of Kato et al.) Preferred stabilization additives are serum albumin, sorbitol and heparin.

A preferred ratio of neurotrophic factor to additive is from about 10:1 to 1:10. A most preferred range of neurotrophic factor to additive is from about 5:1 to 1:5. A most preferred ratio is about 1:1.

One embodiment of this invention is a pharmaceutical composition of bFGF in an aqueous solution suitable for intravenous administration. A preferred embodiment is a pharmaceutical composition comprising bFGF and sorbitol. The preferred composition comprises bFGF, sodium citrate, sodium chloride and sorbitol. A more preferred embodiment is a pharmaceutical composition comprising bFGF with sorbitol in a ratio between 3:1 to 1:3 by weight. The most preferred embodiment contains bFGF and sorbitol in a 1:1 weight ratio. Another preferred composition comprises NGF, sodium acetate, sodium chloride and serum albumin.

One method of administering the pharmaceutical composition is by intravenous injection, but an intravenous infusion is also envisioned. A composition containing one or more neurotrophic factors in an aqueous solution may be administered as a bolus injection, or a series of injections. The administration may be once or several times a day.

The present invention includes all forms of parenteral administration, including without limitation, intravenous, intraperitoneal, intramuscular and subcutaneous means of administration. Also included within the scope of this invention are implantable polymer or membrane devices in which the neurotrophic factor is encapsulated or cells secreting the neurotrophic factor are encapsulated. Such implantable devices can be placed within the patient's brain or other appropriate locations in the body.

A multitude of diseases and disorders may cause neuronal damage, in addition to affecting other types of cells and may be treated by the compositions and methods of this invention. The following is intended to indicate the breadth of diseases and disorders, including stroke and cardiac arrest, which cause neuronal damage and for which the present pharmaceutical composition or the present method can be used.

Ischemia is a deficiency of blood in a tissue, due to functional constriction or actual obstruction of a blood vessel. Ischemia may be caused by stroke or cardiac arrest. Hypoxia, also known as anoxia, is the reduction of oxygen supply to a tissue below physiological levels.

An important distinction should be made between global and focal cerebral ischemia. Focal ischemia, the cause of at least 500,000 cases of "stroke" seen every year in the United States, results from the blockage of a single artery in the brain, resulting in the death of all cellular elements (pannecrosis) in the territory supplied by that artery. Global ischemia, on the other hand, results from general diminution of blood flow to the entire brain or forebrain, and causes the delayed death of neurons in the "selectively vulnerable" regions throughout the brain. The pathology in each of these cases is quite different, as are the clinical correlates. Models of focal ischemia apply to patients with focal cerebral infarction, and models of global ischemia are analogous to cardiac arrest, and other causes of systemic hypotension. It is not generally anticipated that a therapeutic would be effective in treating both global and focal ischemic injury.

Infarction of the brain, due to focal ischemia, results when the blood supply to a localized area is deprived so that damage occurs to neuronal tissue. An infarct is an area of coagulation necrosis in a tissue resulting from obstruction of circulation to the area, most commonly by a thrombus or embolus. An infarct is caused by a deprivation of blood to a given area and may be either ischemic or hemorrhagic. The effect of cerebral ischemia or hypoxia on neuronal cells depends upon its intensity and duration and the maintenance of an effective systemic circulation by shunting blood from other regions of the brain. Common causes of brain infarcts are emboli within cerebral vessels, arteriosclerotic vascular disease and the inflammatory processes, which frequently occur when thrombi form in the lumen of inflamed vessels. Common causes of hemorrhage into the brain are hypertension, hypertensive cerebral vascular disease, trauma rupture of aneurysms, angiomas, blood dyscrasias and bleeding from tumors. Of these, hypertension is the most common cause (Kandel, E. R., Schwartz, J. H., Jessell, T. M., *Principles of Neural Science*, 3rd Ed. (1991) Elsevier Science Publishing Co., Inc., 1041–1049).

While not wishing to be bound by any theory, it is thought that cranial injury, resulting from stroke or cardiac arrest, causing hypoxia or ischemia and neurodegeneration, may make the blood-brain barrier more permeable allowing entry into the CSF of large molecules and even highly charged molecules which normally do not cross the barrier. It is known that upon injury, cells such as neutrophils and monocytes are able to enter the CSF.

Animal models have been developed which attempt to simulate neuronal damage produced by naturally occurring ischemia, hypoxia or neurodegeneration in humans as a means to study these conditions and to study treatments to prevent neuronal cell damage. Some global models induce neuronal damage by artificially reducing the flow of oxygen for a predetermined period of time (Pulsinelli, W. A., et al., *Ann Neurol.*, 11:491–498, 1982). In other focal models of ischemia, a blood vessel is permanently occluded (Finklestein, S. et al. *Stroke*, 21:III-122–III-124, 1990; Chen, S. et al. *Stroke*, 17:738–743, 1986. By carefully monitoring the conditions imposed, the location and extent of expected infarcted material can be determined. Using these models, reproducible neuronal and glial cell damage can be achieved, thereby enabling the study of the efficacy of proposed pharmaceutical compositions as treatments of neuronal damage due to ischemia.

One model of ischemic damage is the mouse middle carotid artery occlusion model (MCA), which is a focal ischemia model (Gotti, B., et al., *Brain Res.*, 522:290–307, 1990, which is incorporated by reference herein in full). Another is the rat four vessel occlusion global model (Alps, B. J., et al., *Neurol.*, 37:809–814, 1987, which is incorporated by reference herein in full).

As described above, ischemic injury may be global or focal, that is, the areas of oxygen deprivation may include the entire brain or just local areas respectively. Focal ischemia injury may be permanent, i.e., where a single artery is permanently occluded, or temporary where the occlusion is removed after a period of time. The effects of ischemic injury may be different depending on the type of ischemic event involved.

Methods to quantify the extent of cerebral ischemic damage are well known to those skilled in the art. One response to ischemic injury is the invasion of glial cells and macrophages into the area of injury, which have significantly greater numbers of $\omega_3$ sites than neurons. After ischemic injury, there is a significant increase in the density of $\omega_3$ (peripheral-type benzodiazepine) binding sites (Benavides, J., et al., *Brain Res.*, 522:275–289 (1990)). One method to detect the presence of $\omega_3$ sites is binding assays using [$^3$H]-PK 11195 (New England Nuclear) (Gotti, B., et al., *Brain Res.*, 522:290–307, 1990, which is incorporated by reference herein in full). Another method of assessing neuronal damage is to determine ischemic cell change (ICC) (Brown, A., et al., *Br. J. Exp. Pathol.*, 49:87–106, 1968, and Pulsinelli, N. A., et al., *Stroke*, 10:267–272, 1979, which are incorporated by reference herein in full).

The examples found below are illustrative of different aspects of the present invention, each demonstrating the effectiveness of the method of treatment described herein employing different conditions of treatment or different animal models. Example 1 describes the intravenous administration of bFGF and NGF in the mouse middle cerebral artery occlusion model. In this focal model of ischemia, the middle cerebral artery is permanently occluded. The results of this experiment, which are tabulated in Table 1, show that the administration of either bFGF or NGF beginning 15 minutes after ischemia resulted in a reduction of ischemic damage in the appropriate dosage ranges.

In Example 2, the rat four vessel occlusion global model was used, and the neurotrophic factor examined was bFGF. This is a model of forebrain ischemia where the carotid arteries are occluded temporarily. Again, bFGF administration was begun shortly following the termination of the ischemic event, and some ischemia damage was prevented. The results of these experiments are tabulated in Tables 2 and 3.

Examples 3 and 4 describe the use of CNTF in the models described in Examples 1 and 2 respectively. Example 5 describes further experiments utilizing the procedures described in Example 1. However, in this example, for one subset of mice the administration of bFGF was not initiated until 6 hours after ischemia. Although the ischemic damage was more effectively prevented by a more timely administration of bFGF, the results suggest that the initiation of administration may be at least as long as 6 hours post ischemia. The results of these experiments are presented in Table 4.

Example 6 employs the bicarotid occlusion model in gerbils. This is also a global ischemia model where both common carotid arteries are occluded temporarily. Ischemic injury was measured by assessing the number of surviving pyramidal neurons in the CA1 region in the hippocampus and by measuring the ischemia-induced increase in hyperactivity. bFGF was administered intravenously either as a bolus injection or by continuous infusion. It was shown that bFGF was effective in preventing ischemia damage, even in cases where the onset of administration was delayed by as much as 6 hours post ischemia. The results of these experiments are depicted in FIGS. 1–5.

In Example 7, bFGF was administered intraventricularly in a rat focal ischemia model. Again, it was found that the administration of bFGF prevented some damage resulting from the ischemia. The results of these experiments are depicted in Table 5 and FIG. 6.

In summary, the Examples presented below show that pretreatment or post treatment with a low dose of intravenously or intraventricularly administered bFGF reduces ischemic damage in a number of models. Although not limited by theory, it is likely that the effects of bFGF in reducing damage after ischemia were due directly to its potent trophic effects on brain cells, especially neurons. High affinity receptors for bFGF are widely distributed on rat brain neurons, including those in cerebral cortex. bFGF is neurotrophic for a wide variety of brain neurons in vitro (including cortical neurons), and protects cultured neurons against several neurotoxins, including EAAs, $Ca^{2+}$ ionophore, and hypoglycemia. (Mattson, *Adv. Exp. Med. Biol.*, 268:211–220, 1990.) Since failure of substrate delivery and EAA toxicity with resulting $Ca^{2+}$ entry into cells appear to be critical processes for neuronal death after ischemia, it is likely that the infarct-reducing effects of bFGF are due, in part, to protection of vulnerable brain neurons, especially those at the borders ("penumbra") of cerebral infarcts. The neuroprotective effects of bFGF in vitro appear to depend on new gene transcription and protein synthesis. It is thus likely that bFGF "switches on" a program of neuronal gene expression resulting in the synthesis of "neuroprotective" proteins, and making the neurons more resistant to ischemia. Such proteins might include heat shock proteins, $Ca^{2+}$ buffering proteins, or $Ca^{2+}/Na^{+}$ extrusion pumps. Moreover, the program of gene expression initiated by bFGF may antagonize active "cell death" programs initiated in response to ischemia.

In addition to its trophic properties on neurons, bFGF might also reduce ischemic damage through its trophic effects on brain glial cells and blood vessels. bFGF is a potent "gliotrophic" factor that promotes the proliferation of brain glial cells (including astroglia and oligodendroglia), as well as an "angiogenic" factor that promotes the proliferation of brain capillary endothelial cells and blood vessels. Thus, bFGF might protect tissue from ischemia through activation of glial cells (in turn secreting other neurotrophic factors), or through formation of new brain capillaries making tissue more resistant to ischemia.

A third potential mechanism of bFGF neuroprotection after ischemia is alteration of systemic physiological parameters leading to decreased infarct size. Cuevas et al. *Science*, 254:1208–1210, 1991, reported that the intravenous administration of bFGF lowered blood pressure in mature rats and rabbits. However, decreased blood pressure, if it occurred, might be expected to increase infarct volume after focal cerebral ischemia. Finally, a small but significant increase in postoperative weight loss was found among bFGF-treated animals in Example 7 Expt. B, and a trend toward increased weight loss was found in Expt. A. bFGF and its receptor are localized in rat hypothalamus, and intraventricular administration of bFGF has been reported to decrease food intake in mature rats. It is possible that bFGF-induced changes in food, water, or electrolyte regulation might have influenced infarct size after focal ischemia.

It has been shown that endogenous bFGF levels increase (ca. 1.5-fold) in tissue surrounding focal cortical infarcts in the mature rat brain, reaching a peak at 2–3 weeks after stroke. (Finklestein, S. et al. *Stroke*, 21-III-122-III-124, 1990.) This "late" endogenous bFGF response may play an important role in wound healing, synaptic reorganization, and subsequent functional recovery after stroke. The results shown here demonstrate that exogenous administration of bFGF appears to be useful as a pharmacological agent to limit the extent of initial neural damage after ischemia.

The following examples are illustrative and are not intended to limit the scope of the invention:

EXAMPLE 1

FOCAL ISCHEMIA MODEL OF CEREBRAL ARTERY OCCLUSION IN MICE

The mouse middle cerebral artery occlusion model, MCA, is a focal ischemia model that has been used to demonstrate the efficacy of bFGF and NGF in treatment of neuronal damage. A radiolabeled marker for glial cell and macrophage infiltration, [3H]-PK-11195 was used in a binding assay to determine the extent of damage. The protocol used was adopted from Gotti, B., et al., *Brain Res.*, 522:290–307, 1990, and describes the marker, PK-11195, in greater detail.

The results show that intravenous administration of bFGF in an aqueous solution containing the additive heparin and NGF in an aqueous solution containing the additive serum albumin afford partial protection to the cerebral cortex from the effects of ischemia induced by permanent occlusion of the middle cerebral artery in the mouse.

Procedure

Adult male mice ($CD_1$ strain), weighing 30–40 g, were anaesthetized by an intraperitoneal (i.p.) injection of 0.1 ml 30 mg/ml pentobarbitone sodium (3 mg) or 5% Halothane in a 70%:30% Nitrous oxide:oxygen gas mixture.

The middle cerebral artery was exposed through a curved incision midway between the eye and the external auditory meatus. The artery was sealed by thermocautery.

The dosing schedule was as follows. The first daily intravenous dose of either 1.5 µg, 15 µg, or 150 µg recombinantly produced human bFGF, 565 µg recombinantly produced human NGF or placebo (all in 0.1 ml volumes) was administered about 15 minutes after ischemia. The mice were then allowed to survive for seven days, during which single daily intravenous doses of the same amount of either bFGF, NGF or placebo were administered. The intravenous solution of bFGF contained 50 mM sodium acetate, 100 mM sodium chloride, at pH 5.0. The bFGF solutions contained an equal amount of heparin as the bFGF. The intravenous solution of NGF contained 10 mM sodium citrate, pH 6.0, 150 mM sodium chloride in 0.1% human serum albumin. The total dosages ranges for the mice was 37.5 µg/kg, 375 µg/kg and 3.75 mg/kg bFGF and 14.325 mg/kg NFG.

The animals were sacrificed 24 hours after the last dose. The infarcted area was dissected from the infarcted hemisphere and the contralateral area was also taken as control tissue.

Damage in the ischemic hemisphere was quantified by measuring the binding of [3H]-PK-11195, which provides an index of ischemic damage insofar as an increase in binding of [3H]-PK-11195 (assessed by $B_{max}$) reflects neuronal damage. Compounds which prevent the increase in the number of binding sites are considered neuroprotective.

Results

The results of bFGF and NGF are given in Table 1.

TABLE 1

The effect of bFGF and NGF in the MMCa-occlusion model

| Treatment | n | Isc kd | MonIsc Kd | Isc Bmax | NonIsc Bmax | % inc L/R | % DAMAGE |
|---|---|---|---|---|---|---|---|
| Placebo | 7 | 0.35 ± 0.09 | 0.31 ± 0.09 | 741 ± 166 | 316 ± 111 | 277 ± 125 | 100 |
| 1.5 μg bFGF | 6 | 0.47 ± 0.10 | 0.31 ± 0.12 | 644 ± 171 | 225 ± 64 | 387 ± 284 | 99 |
| 15 μg bFGF | 5 | 0.42 ± 0.04 | 0.22 ± 0.06 | 529 ± 98 | 218 ± 69 | 217 ± 79 | 73 |
| 150 μg bFGF | 6 | 0.20 ± 0.03 | 0.26 ± 0.07 | 147 ± 23** | 222 ± 57 | −16 ± 17** | 0 |
| 565 μg NGF | 4 | 0.31 ± 0.13 | 0.37 ± 0.11 | 287 ± 144* | 243 ± 128 | 23 ± 4* | 10 |

ANOVA Dunnett's test difference from placebo
*0.05 > p < 0.1
**p < 0.01

Animals treated with placebo showing an increase in the $B_{max}$ of [$^3$H]-PK-11195 binding in the ischemic hemisphere resulting in an increase in the ratio of binding of the left (L, ischemic) hemisphere; right (R, non-ischemic) hemisphere. This was taken as 100% damage against which drug effects could be calculated. 15 μg bFGF (375 μg/kg) produced a small but non-significant reduction in ischemic damage, however, 150μg bFGF (3.75 mg/kg) produced a total (100%) protection. 565 μg NGF (14.325 mg/kg) also showed protective effects in this model.

There were no changes in the affinity of [$^3$H]PK-11195 for its binding sites in the study as assessed by $K_d$.

EXAMPLE 2

RAT GLOBAL ISCHEMIA MODEL OF FOUR-VESSEL OCCLUSION FOR GLOBAL ISCHEMIA

The rat four vessel occlusion model (4VO) was developed to quantify neuronal damage, based on light microscopy assessment of morphological changes. Comparisons of morphology are made in the presence and absence of drug treatment. The duration of ischemic injury has been modified to particularly affect hippocampal CA1 neurons.

Procedure

Experimental conditions were based on those described in Alps, B. J., and Hass, W. K., Neurol., 37:809–814 (1987).

Briefly, the rats were anesthetized with Ketamine HCL (5 mg/ml, IM) and 1–2% halothane. The vertebral arteries were sealed with electrocautery following the procedure outlined in Pulsinelli, W. A. and Briefly, J. B., Stroke, 10(3):267–272 (1979).

After fasting for 24 hours following sealing of the vertebral arteries, the animals were reanesthetized. During this procedure, a bitemporal electroencephalogram (EEG) was recorded continuously. Blood pressure (BP) was recorded from a tail artery and the two common carotid arteries were exposed for temporary occlusion.

Induction of Forebrain Ischemia

Forebrain ischemia was induced by a 10 minute occlusion of both common carotid arteries. During the 10 minute carotid artery occlusion, the anaesthetic concentration was varied upward or downward to hold BP at about 50 mmHg.

Rectal temperature was measured using a digital thermometer probe following surgical repairs prior to returning the animals to their cages for recovery. Prior to this application and following the release of the carotid artery occlusion, blood glucose was measured from an arterial sample using a Reflolux-S glucose meter (Boehringer Co [London] Ltd., UK).

Drugs, Solutions, Placebo and Treatment Regimen

Recombinantly produced human bFGF material was administered in an aqueous solution containing 100 μg/ml bFGF and 100 μg/ml heparin (Synergen, Inc., Boulder, Colo., commercially available from R&D Systems), dissolved in buffer comprising 10 mM sodium citrate (pH 6.0), 150 mM sodium chloride, and 0.1% rat serum albumin. The placebo formulation given to control animals was 10 mM citrate (pH 6.0), 150 mM NaCl, 0.1% rat serum albumin.

Animals were dosed at 15 μg/kg intravenously via a tail vein within 5 minutes of carotid artery reperfusion and this dose was repeated twice daily intravenously for three days.

Termination Procedure

At 72 hours post-ischemia each animal was deeply anaesthetized with sodium pentobarbitone and thorocotomised. The cerebral circulation was washed out with heparinized saline via cardiac puncture and the brain was then perfused-fixed with a 10% formalin saline solution.

Neuropathological Grading System and Quantification of Damage

Neuropathological damage was assessed in terms of ischemic cell change (ICC) as described by Brown, A., and Brierley, T. B., Br. J. Exp. Pathol., 49:87–106 (1968). Specific areas examined included:

1. Layers I-VI of the striatal cortex overlying the striatum (anterior neocortex)
2. Layers I-VI of the hippocampal cortex overlying the hippocampus (posterior neocortex)
3. The hippocampal CA1 subfield
4. The thalamus
5. The striatum
6. The cerebellar Purkinje cells and brain stem cells Each area was graded for ICC on the basis of the following values in a manner adapted from that reported by Pulsinelli, N. A., and Brierley, J. B., Stroke, 10:267–272 (1979), which is incorporated in full. Briefly, ICC changes include:

Score 0=Normal
0–1=0–10% ICC
1–2=10–25% ICC
2–3=25–50% ICC
3–4=50–100% ICC

The scores for the hippocampal CA1 subfield, striatum and thalamus were assessed separately for each hemisphere and the mean values derived. The cerebellar Purkinje cells were scored for the single structure in each animal. Thus, for each animal a whole brain score was calculated from the mean of six regional values and then averaged to give a group mean score both including and omitting the CA1 component. An absolute cell count was also made for the CA1 subfield.

General Hemodynamic Data for Blood Pressure, Body Temperature and Blood Glucose

Blood pressure was measured but did not change. Data for the blood pressure in the rat is presented in Table 2.

TABLE 2

BLOOD PRESSURE (STYSTOLIC/DIASTOLIC BP) (mmHg)
IN RATS SUBJECTED TO 10 MIN. FOREBRAIN ISCHEMIA

| Group | Starting BP | Pre-occlusion BP | Peak Pressor BP | Isoelectric EEG BP | Return to EEG BP | Final BP |
|---|---|---|---|---|---|---|
| Drug-treated bFGF (n = 6) | *85.8 ± 5.4<br>**80.8 ± 5.4 | 75.8 ± 6.9<br>70.8 ± 6.9 | 109.0 ± 8.1<br>104.5 ± 8.5 | 75.8 ± 14.1<br>70.8 ± 14.1 | 118.3 ± 5.9<br>113.3 ± 5.9 | 118.3 ± 5.9<br>113.3 ± 5.9 |
| Vehicle Controls (n = 5) | *85.4 ± 3.2<br>**82.4 ± 4.0 | 77.0 ± 7.2<br>72.0 ± 7.2 | 106.0 ± 6.8<br>101.0 ± 6.8 | 97.0 ± 13.2<br>92.0 ± 13.2 | 129.0 ± 4.3<br>124.0 ± 4.3 | 133.0 ± 2.5<br>128.0 ± 2.5 |

*systolic
**diastolic

Rectal body temperatures measured at the end of ischemia were acceptable, with no evidence of hypothermia nor hyperthermia. The mean drug-treated animal temperature was 37.7°±0.12° C. and for vehicle controls was 37.9°±0.18° C.

Blood glucose levels were unaffected by the procedure in either group, where the drug-treated animals showed a pre-ischemia value of 7.5±0.2 mM and post-ischemia value of 7.0±0.3 mM, and where these respective values for vehicle controls were 7.6±0.5 mM and 7.5±0.3 mM.

Neuropathological Findings and ICC Scores

Data for the effects of bFGF against ICC compared to untreated controls is presented in Table 3. Data for normal brains is also included in Table 3 to indicate the background level for artifact staining.

degeneration which occurs over three days following an ischemic insult in the rat and that the compound may be effective in several brain areas.

Morphological assessment of brain slices demonstrated that intravenous administration of neurotrophic factors partially protected hippocampal CA1 neurons in the rat 4VO model, as were the regions including the anterior and posterior neocortex, thalamus, striatum and cerebellar Purkinje cells, against ischemia-induced damage (Table 3).

EXAMPLE 3

ADMINISTRATION OF CNTF IN THE MOUSE FOCAL ISCHEMIA MCA MODEL

The effects of CNTF are studied in the mouse MCA occlusion model essentially following the procedure set

TABLE 3

NEUROPATHOLOGICAL SCORES (0-4) FOR ISCHEMICA CELL CHANGE IN RATS
SUBJECTED TO FOUR VESSEL OCCLUSION AND TREATED WITH bFGF VERSUS DRUG VEHICLE ALONE

| Group | Hippocampal $CA_1$ Cells | Posterior Neocortex | Anterior Neocortex | Thalamus | Striatum | Cerebellar Purkinje Cells | Mean Brain Score $+CA_1$ | Mean Brain Score $-CA_1$ |
|---|---|---|---|---|---|---|---|---|
| Control n = 5 | 4.00 ± 0.00 | 1.40 ± 0.20 | 1.15 ± 0.20 | 1.60 ± 0.20 | 1.35 ± 0.20 | 1.70 ± 0.30 | 1.85 ± 0.10 | 1.44 ± 0.11 |
| bFGF (n = 6) | 2.58 ± 0.63 | 0.75 ± 0.26 | 0.92 ± 0.15 | 0.71 ± 0.48 | 0.50 ± 0.34 | 1.17 ± 0.53 | 1.10* ± 0.31 | 0.81 ± 0.33 |
| % Control Score | 64.5% | 53.6% | 80.0% | 44.4% | 37.0% | 68.8% | 58.1 ± 6.6% | 56.8 ± 7.5% |
| Normal (n = 6) | 0.33 ± 0.11 | 0.31 ± 0.06 | 0.36 ± 0.12 | 0.79 ± 0.19 | 0.79 ± 0.19 | 0.50 ± 0.18 | 0.52 ± 0.09 | 0.55 ± 0.09 |

*Statistical Significance P <0.05 (t-test)

The hippocampal CA1 neurons were partially protected in animals treated with bFGF compared to surviving controls, which all showed maximal damage on subjective scoring, thus there was no standard error and the region was re-evaluated by an absolute cell count. The percentage of abnormal neurons in the vehicle control group was 97.7±0.8% ICC (n=5) and the bFGF-treated group was 56.6±16.8% ICC (n=6) (p<0.5 t-test). All other brain areas examined showed partial protection for bFGF. Overall, the drug-treated group showed 58.1±6.6% of the level of the control group mean brain score for damage with the CA1 component value included and 56.8±7.9% in the absence of the CA1 value. Protection for the thalamus and striatum compared favorably against ICC scores for normal brains. These data show that bFGF administered intravenously prevents or reduces the incidence of delayed neuronal forth in Example 1. CNTF is studied in these animal models using pharmaceutically acceptable compositions in the following daily amounts, 1 µg, 10 µg or 100 µg. The amount of CNTF may be adjusted to provide equivalent dosages according to the weight of the individual being treated.

EXAMPLE 4

ADMINISTRATION OF CNTF IN THE RAT GLOBAL ISCHEMIA 4VO MODEL

The effects of CNTF are studied in the rat 4VO model essentially following the procedure set forth in Example 2. CNTF is studied in these animal models using pharmaceutically acceptable compositions in the following daily amounts, 1 µg, 10 µg, or 100 µg. The amount of CNTF may be adjusted to provide equivalent dosages according to the weight of the individual being treated.

EXAMPLE 5

DELAYED bFGF ADMINISTRATION IN MCA MODEL OF FOCAL ISCHEMIA IN MICE

The middle carotid artery occlusion model (MCA) of focal ischemia as described in Example 1 was performed to determine if the delayed administration of bFGF could reduce ischemic damage. The results of this series of experiments are summarized in Table 4. Results are given for mice that were given intravenously a placebo after the ischemic event, mice given intravenously 100μg of bFGF 15 minutes, 24 h and 48 h post-ischemia, and mice given intravenously 100 μg of bFGF 6 h, 24 h and 48 h post-ischemia.

Consistent with the results shown in Example 1, mice given bFGF shortly after the ischemia event were strongly protected from neuronal damage. Those mice given their first dose of bFGF 6 hours post-ischemia were also provided some protection from neuronal damage.

The measure of % damage as given in Table 4, is an index of protection which takes into consideration both the absolute values and the % increase L/R; any changes in right hemisphere are corrected for % damage =(left$_t$–right$_t$/left$_c$–right$_c$) % where c is the control (placebo) group and t is the treatment group.

TABLE 4

| | | Bmax | | % increase | |
|---|---|---|---|---|---|
| | n | left | right | L/R | % damage |
| Placebo | 9 | 577 ± 128 | 128 ± 34 | 699 ± 365 | 100 |
| 100 μg bFGF (15 min, 24 h, 48 h) | 10 | 220 ± 60 | 107 ± 19 | 99 ± 38 | 25 |
| 100 μg bFGF (6 h, 24 h, 48 h) | 10 | 495 ± 103 | 166 ± 31 | 294 ± 120 | 73 |

EXAMPLE 6

EFFECTS OF INTRAVENOUSLY ADMINISTERED bFGF ON GLOBAL ISCHEMIC INJURY IN THE GERBIL

The mongolian gerbil is a useful model for studying ischemic injury. Ischemic injury can be induced by occluding blood flow through both common carotid arteries (bicarotid occlusion, BCO) since there is an incomplete circle of Willis connecting the carotid and vertebrobasilar arteries. Neurons in the CA1 region in the hippocampus of gerbils are selectively vulnerable to ischemia and undergo a slow process of delayed neuronal degeneration. Depending upon the duration of bicarotid occlusion, other forebrain structures such as the striatum, thalamus, and neocortical layers 3 and 5 may also be damaged. In this example, the effect of intravenously administered bFGF was tested on two ischemic injury parameters; 1) an ischemia-induced decrease in the number of surviving pyramidal neurons in the CA1 region in the hippocampus and 2) an ischemia-induced increase in hyperactivity in an open-field chamber.

In this example, the intravenous injection of bFGF is judged to be neuroprotective if treated gerbils meet the following criteria; 1) there is a bFGF-induced increase in the number of neurons in histological sections of hippocampus taken at seven days post ischemia; and 2) there is a bFGF-induced decrease in an abnormal ischemia-induced behavioral parameter, hyperactivity in an open-field chamber.

Lesioning of the hippocampus causes impaired spatial learning in monkeys and rats. In the gerbil, transient forebrain ischemia causes an impairment in spatial mapping such that gerbils with ischemic injury display persistent exploration of a test environment (Chandler, M. J. *Pharm. Meth.* 14:137–146, 1985 and Wang, D. *Brain Research,* 533:78–82, 1990). The increase in exploratory behavior in an open-field chamber reflects the impaired ability of an ischemia-injured gerbil to make a mental map of a novel environment. Thus, the measurement of open-field activity after ischemia allows the assessment of cognitive functions in the hippocampus and supports the assessment of histological preservation of hippocampal neurons.

Ischemic Injury

On the day before the global ischemia, gerbils were anesthetized with isoflurane/oxygen and a ventral midline incision was made in the cervical region. Both carotid arteries were identified and loosely looped with silk suture. The external jugular vein was cannulated unilaterally with polyethylene tubing. The tubing was exteriorized at the nape of the neck to facilitate the intravenous injection of bFGF or vehicle. On the following day, the instrumented gerbils were anesthetized with isoflurane/oxygen and the cervical incision was reopened. The right and left common carotid arteries were identified by the presence of the looped silk suture and were occluded for 2 min 25 sec with microaneurysm clips. Throughout the ischemia, body temperature was maintained at 37.5° C. After blood flow was reestablished through the carotid arteries and the cervical incision was closed, the gerbils were placed for two hours in an incubator that was maintained at 37.5° C. Sham-treated gerbils underwent cannulation of the jugular vein, looping of the carotid arteries, and exteriorization of the carotid arteries without occlusion of blood flow.

Treatment with bFGF bFGF was administered intravenously as either a bolus injection or by continuous infusion. Human recombinant bFGF, from Synergen, Inc., was used in a saline formulation for bolus injection and with sorbitol as a stabilizing agent for infusion. The bolus injections were given to isoflurane-anesthetized gerbils into the jugular vein through the exteriorized polyethylene tubing. The continuous infusion of bFGF into the jugular vein was accomplished by connecting the indwelling polyethylene tubing to a mini-osmotic pump. The gerbils receiving bolus injections were treated three times at approximately 24 hr intervals. The first treatment was given at either 0, +2 hr, +4 hr or +8 hr relative to the bicarotid occlusion. The second and third treatments were given at 24 and 48 hr post bicarotid occlusion. The continuous infusion of drug was at a delivery rate of one microliter per hour from an Alzet 2001 mini-osmotic pump such that a total dose of 1.5 mg bFGF/kg per day was delivered for three days.

Assessment of Ischemic Injury

The activity of the gerbils in an open-field chamber was measured at 96 hr post bicarotid occlusion. The gerbil was placed in the gridded chamber and its movements were recorded for 15 min on a videocamera. Activity was expressed as the number of squares crossed during the final ten min period of observation in the chamber. On day seven, hippocampal tissue was obtained for histological assessment after perfusion fixation of the brain by the intracardiac injection of a buffered formalin solution. Paraffin-embedded sections were stained with cresyl violet. A blinded observer counted the number of histologically preserved neurons in the CA1 region of the right and left hippocampi. The reported values are combined counts from a one mm section from each hemisphere. In vehicle-treated ischemic gerbils, cell loss resulting from necrosis and phagocytosis of the neurons was almost complete from the hypoxia-vulnerable region of the hippocampus. The total number of neurons remaining in vehicle- and bFGF-treated gerbils was compared.

Results of Bolus Intravenous Administration of bFGF.

Figure 1B:
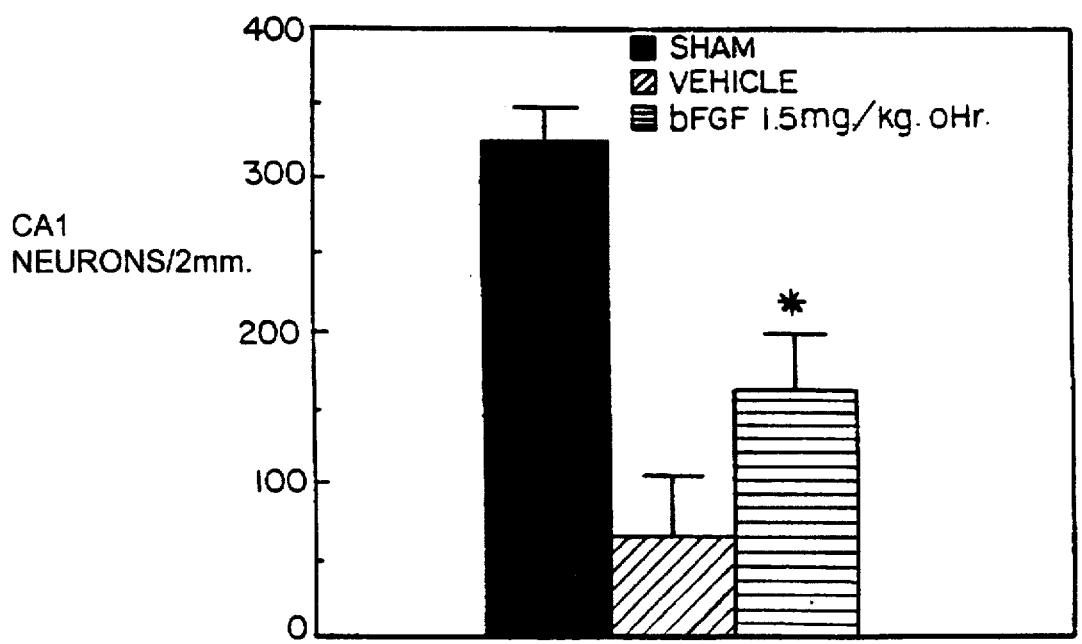
Figure 2:
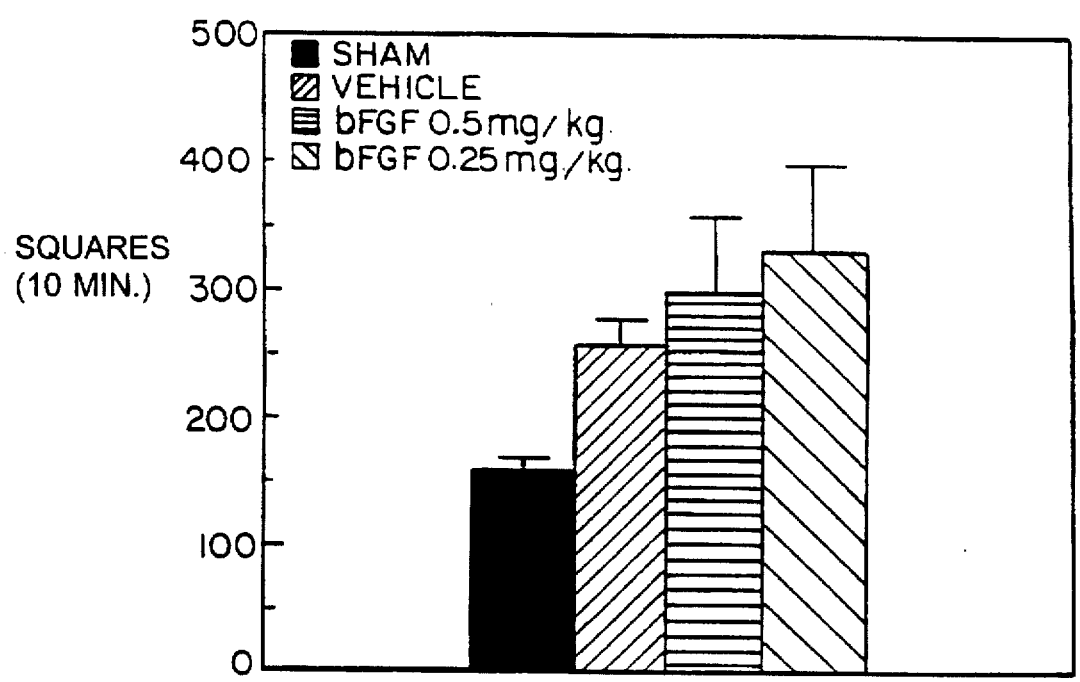
FIG. 2 depicts the effects of three bolus intravenous administrations of bFGF (0.25 or 0.5 mg/kg/injection at 0, 24, and 48 hr post ischemia) on activity in an open field chamber. n=4 (sham), n=5 (vehicle treated), n=9 (bFGF-treated, 0.25 mg/kg), and n=7 (bFGF-treated, 0.5 mg/kg).
Figure 3A:
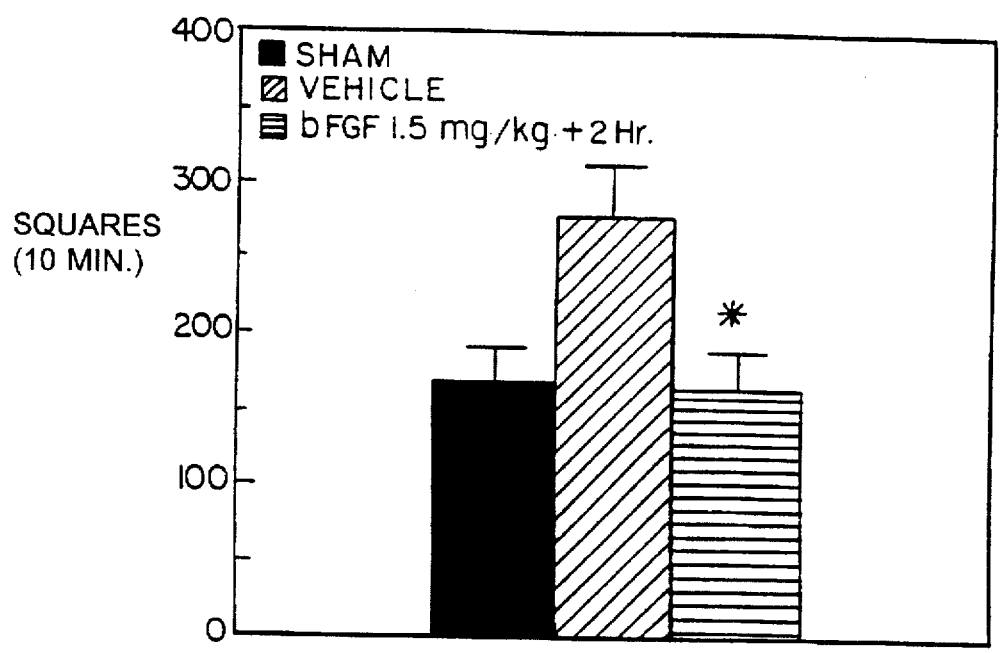
FIG. 3(*a–g*) depicts the effects of three bolus intravenous administrations of bFGF (1.5 mg/kg/injection at 2, 24, and 48 hr post ischemia) on activity in an open field chamber and on the number of surviving hippocampal neurons. * indicates a significant difference between vehicle-treated and bFGF-treated by the unpaired t test (p<0.05) based on the activity parameter by the Mann Whitney test p=0.06 on neuronal counts comparing vehicle- and bFGF-treated gerbils. n=10 (sham), n=17 (vehicle-treated), n=15 (bFGF-treated).
Figure 3B:
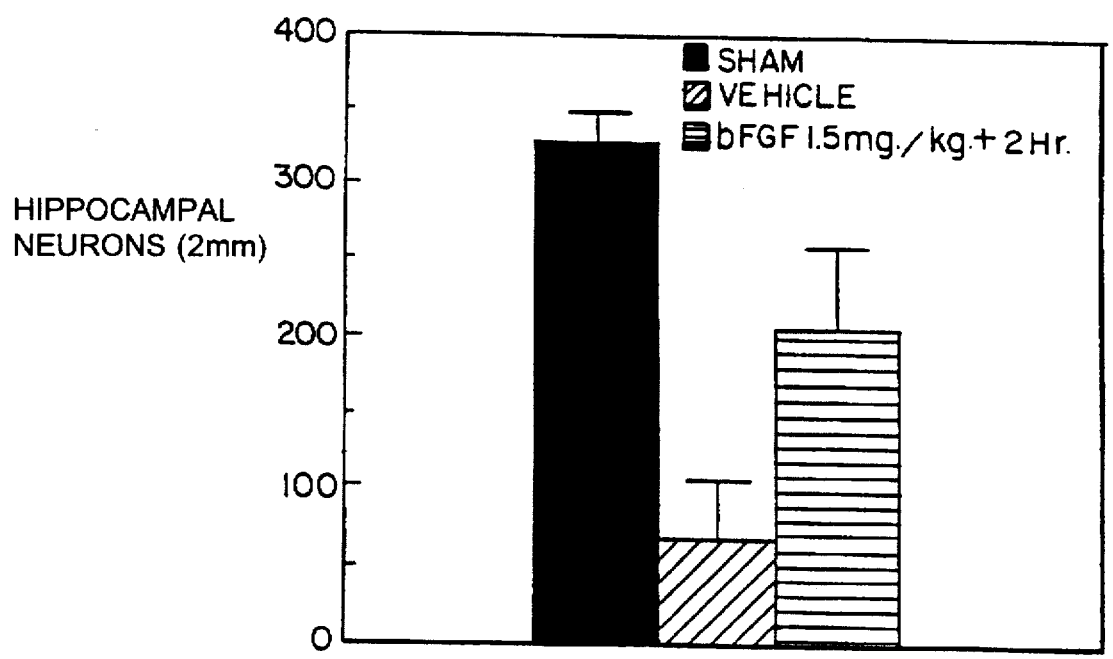
Figure 4:
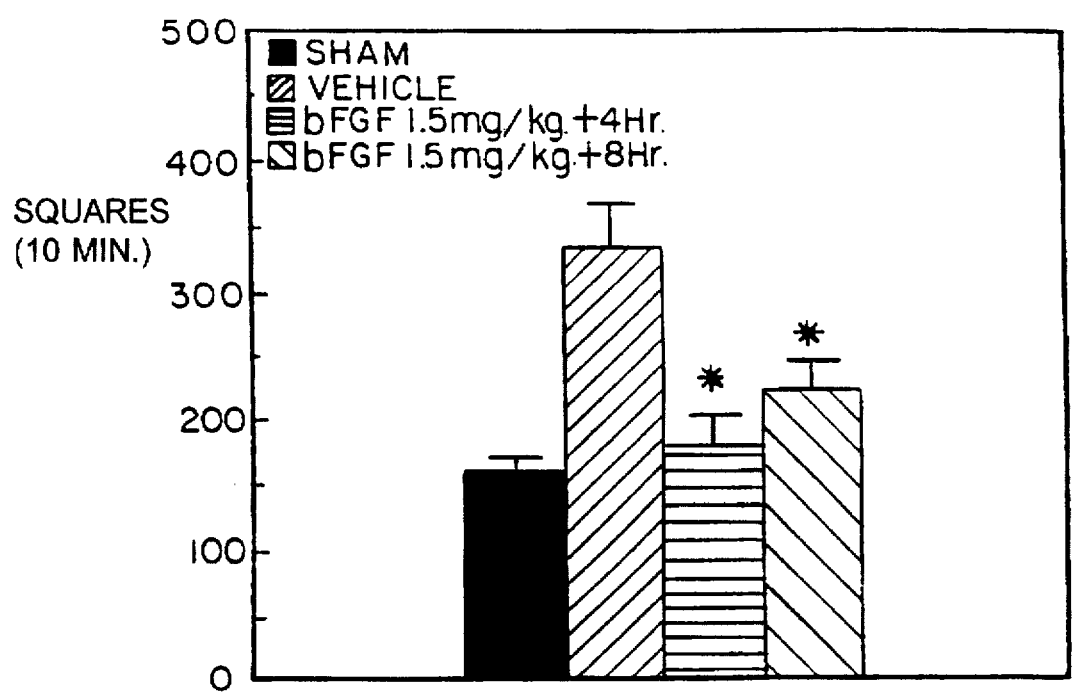
FIG. 4 depicts the effects of three bolus intravenous administrations of bFGF (1.5 mg/kg/injection at 4 or 8 hr, 24, and 48 hr post ischemia) on activity in an open field chamber. * indicates a significant difference between vehicle-treated and bFGF-treated by the unpaired t test (p<0.05). n=16 (sham), n=27 (vehicle treated), n=16 (bFGF-treated at +4 hr), n=21 (bFGF-treated at +8 hr).

The effects of the bolus intravenous administration of bFGF at doses of 0.25, 0.5, and 1.5 mg/kg was tested. The bFGF was administered at 0, 24, and 48 hr post ischemic injury. FIG. 1 shows the effect of the highest dose on ischemia-induced hyperactivity and neuronal loss. At 1.5 mg/kg, bFGF significantly decreased the hyperactivity and increased the number of surviving neurons. At doses of 0.25 and 0.5 mg/kg, treatment with bFGF was not effective in reducing ischemic injury (FIG. 2). The protective effects of bFGF at 1.5 mg/kg when the first treatment was delayed until 2, 4, or 8 hr post ischemia and the second and third treatments with bFGF are given at 24 and 48 hr post ischemia was also tested. At the 2 hr timepoint, bFGF was protective against ischemic injury based on a significant reduction in hyperactivity and a significant salvage of hippocampal neurons (FIG. 3). At the 4 and 8 hr timepoints, bFGF was protective against ischemic injury based on a significant reduction in hyperactivity (FIG. 4).

Results of Continuous Intravenous Infusion of bFGF

Figure 5:
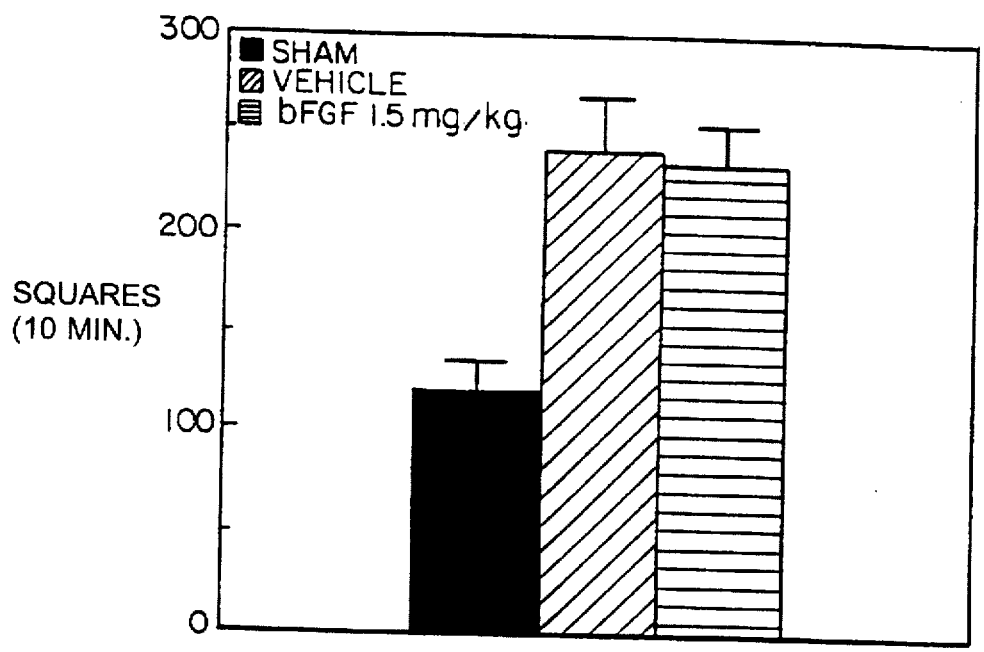
FIG. 5 depicts the effects of the continuous infusion of bFGF (1.5mg/kg/day for 3 days post ischemia) on activity in an open field chamber. n=15 (sham), n=23 (vehicle-treated) and n=20 (bFGF-treated).

The protective effects of bFGF administered by continuous intravenous infusion with the onset of delivery at time zero relative to the ischemic injury and the rate of delivery at 1.5 mg/kg during each 24 hr period was also performed. Under these conditions, bFGF was not protective against ischemic injury when continuously infused based on the hyperactivity parameter (FIG. 5).

EXAMPLE 7 bFGF ADMINISTERED INTRAVENTRICULARLY IN RAT FOCAL ISCHEMIA MODEL

Mature male Long-Evans rats (250–350 g) were anesthetized with sodium pentobarbital (60 mg/kg, i.p.) and placed in a stereotaxic head holder (David Kopf Instruments, Tujuna, Calif.). The dorsal surface of the skull was exposed by midline incision, and a small burr hole (2 mm diameter) was drilled over the right lateral ventricle, 1.6 mm lateral and 0.9 mm posterior to bregma. A stainless steel cannula (I.D. 0.020", O.D. 0.028", 2 cm long) was then inserted stereotaxically into the ventricle to a depth of 4.4 mm beneath the surface of the skull. The tubing was bent at a 90° angle 1–1.5 cm from its tip and connected to polyethylene tubing (I.D. 0.76 mm, O.D. 1.22 mm, 10 cm long) that was connected (by glue) to a mini-osmotic pump (Alzet 1007D, 100 µl fill volume, pump rate =0.5 µl/hr; Alza Corp., Palo Alto, Calif.) implanted subcutaneously in the back. The cannula was fixed to the skull by orthodontic resin (L.D. Culk Co., Milford, Del.) bonded to two small machine screws (⅛" stainless steel slotted) inserted in the skull. The pump, tubing, and cannula were primed before insertion with infusate solutions; a 3-0 nylon suture was inserted into the cannula during implantation to prevent obstruction by brain tissue. The wound was closed with 3-0 silk suture and cefazolin (10 mg, i.m.) was administered). After surgery animals were kept in individual cages and fed soft food.

For Experiment A (Expt. A), pumps were filled with vehicle alone (containing 127 mM NaCl, 2.6 mM KCl, 1.2 mM CaCl$_2$, 0.9 mM MgCl$_2$, 4.14 mM HEPES, 3 mM glycerin, 0.001% bovine serum albumin [BSA], and 0.01% fast green), or vehicle plus bFGF (100 µgm/ml). For Experiment B (Expt. B), pumps were filled with vehicle alone (containing 143 mM NaCl, 2.6 mM KCl, 1.3 mM CaCl$_2$, 0.9 mM MgCl$_2$, 4.6 mM HEPES, 1.0 mM sodium citrate, 0.01% human serum albumin [HSA], and 0.01% fast green), or vehicle plus bFGF (100 µgm/ml) plus heparin (100 µgm/ml), added to stabilize bFGF. At the concentration and pump rate used, bFGF was delivered at 50 ng/hr, or 1.2 µgm/day. For each experiment, the vehicle represented artificial CSF, plus albumin as protein carrier, plus fast green as a dye to visualize cannula placement, plus trace concentrations of buffers present in bFGF stock solutions. The differences in vehicles for Expts. A and B reflect differences in the bFGF stock solutions used in these experiments. Recombinant human bFGF was obtained from Synergen, Inc. (Boulder, Colo.). Each batch of bFGF used was tested for biological activity by standard mitogenic assay on Balb c/3T3 cells (5–10 activity units/ng). The heparin preparation used (porcine intestinal heparin; Biosynth International, Skokie, Ill.) had no biological activity in this assay.

Three days after cannula implantation, animals were reanesthetized with 2% halothane and given atropine (0.15 mg/kg, i.p.). Animals were then intubated and connected to a ventilator (SAR-830; CWE Inc., Ardmore, Pa.) delivering 1% halothane/70% nitrous oxide in oxygen. The right femoral artery and vein were cannulated for monitoring of mean arterial blood pressure (MABP; Gould RS3200 Blood Pressure Monitor, Gould Inc., Valley View, Ohio), drug delivery, and blood sampling. Animals were then paralyzed with pancuronium bromide (0.5 mg/kg, i.v.) Arterial blood gasses (Corning 178 Blood Gas Analyzer, Ciba Corning Diagnostic Corp., Medford, Mass.), blood glucose (Accu-Check Blood Glucose Analyzer, Boehringer Mannheim, Indianapolis, Ind.), and hematocrit were measured at least twice during surgery and the immediate post-operative period. The stroke volume and rate of the ventilator was adjusted to maintain PaO$_2$ between 100–200 mmHg and PaCO$_2$ between 30–40 mm Hg. Core body temperature was monitored by rectal thermocouple (Model 73 ATA, Yellow Springs Instrument Co., Yellow Springs, Ohio) and maintained between 36°–37.5° C. with a homeothermic blanket control unit (Harvard Bioscience, South Natick, Mass.).

Focal ischemic infarcts were made in the right lateral cerebral cortex in the territory of the middle cerebral artery (MCA) by the method of Chen, et al. *Stroke*, 17:738–743, 1986. Both common carotid arteries were exposed by midline ventral incision. The animal was then placed in a stereotaxic head holder, and a 1 cm skin incision was made at the midpoint between the right lateral canthus and the anterior pinna. The temporal muscle was retracted, and a small (3 mm diameter) craniectomy was made at the junction of the zygoma and squamosal bone using a dental drill cooled with saline. Using a dissecting microscope, the dura was opened with fine forceps, and the right MCA was ligated with two 10-0 monofilament nylon ties just above the rhinal fissure and transected between the ties. Both common carotid arteries were then occluded by microaneurysm clips for 45 min. After removal of the clips, return of flow was visualized in the arteries. Anesthesia was maintained for 15 min., and animals were returned to individual cages and fed soft food after surgery.

Twenty four hours after cerebral infarction, animals were again weighed, and then sacrificed by rapid decapitation. In some animals, rectal temperatures was also measured before sacrifice. Brains were removed, inspected visually for anatomy of the MCA as well as for signs of hemorrhage or infection, immersed in cold saline for 10 min., and sectioned into seven standard coronal slices (each 2 mm thick) using a rodent brain matrix slicer (Activational Systems, Warren, Mich.). Brains were also examined visually for the presence of dye (fast green) in the cerebral ventricles, basal cisterns, and over the convexities. Slices were placed in the vital dye, 2,3,5-triphenyl tetrazolium chloride (TTC, 2%; Chemical Dynamics Co., N.J.) at 37° C. in the dark for 30 min., followed by 10% formalin at room temperature overnight. The outline of right and left cerebral hemispheres as well as that of infarcted tissue, clearly visualizable by lack of TCC staining, was outlined on the posterior surface of each slice using an image analyzer (Olympus SZH microscope connected to an MTI videocamera and Sony video monitor; Bioquant IV Image Analysis System run on an EVEREX computer). Both the surgeon and image analyzer operator were blinded to the treatment given each animal.

To test the specific hypothesis that bFGF treatment reduces infarct volume, volume of infarcts among bFGF-vs. vehicle-treated animals were compared by unpaired, two-tailed t-tests for each experiment, and by two-way analysis of variance (ANOVA; Expt. X Treatment) for combined data. Other anatomical and physiological measurements were compared among bFGF-vs. vehicle-treated animals by unpaired, two-tailed t-tests for each experiment, using the Bonferroni correction for multiple pairwise comparisons.

RESULTS

Of 63 animals prepared initially for Expts. A and B, five (8%) died before sacrifice; three (5%) were excluded because of intra-operative hypoxia, hypercapnia, or hypotension; three (5%) were excluded due to lack of dye in ventricles on sacrifice; and four (6%.) were excluded because of anatomical anomalies of the middle cerebral artery ("double MCA") discovered on sacrifice. Data on the remaining 48 animals (76% of total prepared) were taken for analysis. Excluded animals were distributed equally among vehicle- and bFGF-treated animals, and among Expts. A and B.

The model of focal cerebral ischemia used resulted in clearly-visualizable, well-demarcated infarcts in the right lateral cerebral cortex in the territory of the MCA. All brains taken for analysis showed the presence of dye (fast green) in the cerebral ventricles, as well as faint dye in the basal cisterns and over the convexities. No gross infections or hemorrhages into infarcts was found at sacrifice. Overall infarct volume was 110±6 mm$^3$ (mean ±SEM; N=48).

Figure 6:
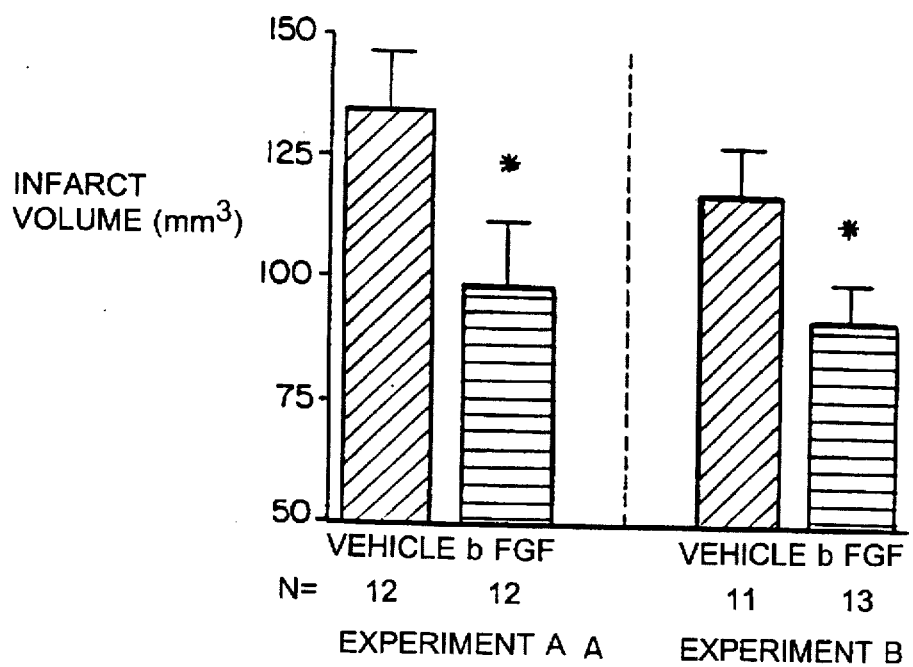
FIG. 6 depicts the infarct volume of rats treated with vehicle and with bFGF as described in Example 7 below.

In Expt. A, infarct volume in animals receiving vehicle alone (N=12) or vehicle plus bFGF (1.2 μgm/day; N=12) was compared. This experiment showed a 27% reduction in infarct volume among bFGF-vs. vehicle-treated animals (98±14 vs. 135±11 mm$^3$ mean ±SEM, respectively; t=2.07, df=22, p=0.05; FIG. 6). In Expt. B, this same dose of bFGF was co-administered with an equivalent dose of heparin, added to stabilize the bFGF. (The heparin preparation used had no FGF-like activity as assessed by standard Balb c/3T3 mitogenic assay, and, at the low dose administered, we found no evidence of the anticoagulant effects of heparin in terms of macro- or micro-hemorrhage into infarcts.) Expt. B showed a 21% reduction in infarct size among bFGF/heparin (N=13) vs. vehicle-treated (N=11) animals (92±7 vs 117±10 mm$^3$, mean±SEM, respectively; t=2.11, df=22, p=0.05; FIG. 1). Differences in infarct volumes for Expts. A and B were not accounted for by differences in right hemisphere or total brain volume among animals (Table 5).

A two-way ANOVA showed no effect of experiment on lesion volume (F[1/44]=1.22,p-n.s.), or interaction between experiment and treatment (F[1/44]=0.29,p-n.s.), but did confirm an overall treatment effect in favor of bFGF (25% reduction in infarct volume; 126±8 vs. 95±7 mm$^3$ for vehicle-[N=23] vs. bFGF-treated animals [N=25], respectively; F[1/44]=8.35, p=0.006).

No differences in intraoperative MABP, arterial PaO$_2$, PaCO$_2$ or pH, blood glucose, hematocrit, or core temperature were found among vehicle- vs. bFGF-treated animals for Expt. A or B (Table 5). Moreover, we found no differences in postoperative core temperature in a random subset of vehicle- vs. bFGF-treated animals in Expt. B (37.8±0.1 [N=4] vs. 37.4±0.1° C. [N=5], respectively; t=1.81, df=7, p-n.s.). A small (14%) but significant increase in postoperative weight loss was found among bFGF-treated animals in Expt. B, and there was a trend toward increased weight loss in Expt. B (Table 5). However, the magnitude of postoperative weight loss was not correlated with infarct volume either for Expt. B alone (r=0.314, p-n.s.; N=24), or for the combined results (r=0.035, p-n.s.; N=48).

TABLE 5

|  | EXPT. A | | EXPT. B | |
| --- | --- | --- | --- | --- |
|  | Vehicle (N = 12) | bFGF (N = 12) | Vehicle (N = 11) | bFGF (N = 13) |
| Preoperative | | | | |
| Weight (gm) | 288 ± 8 | 292 ± 6 | 284 ± 6 | 280 ± 6 |
| Intra-operative | | | | |
| MABP (mm Hg) | 106 ± 4 | 113 ± 4 | 110 ± 4 | 123 ± 2 |
| PaO2 (torr) | 145 ± 6 | 147 ± 6 | 172 ± 7 | 165 ± 7 |
| PaCO2 (torr) | 34 ± 1 | 35 ± 1 | 35 ± 1 | 33 ± 1 |
| pH | 7.39 ± .01 | 7.42 ± .01 | 7.43 ± .01 | 7.44 ± .01 |
| Glucose (gm/dl) | 126 ± 2 | 128 ± 4 | 137 ± 7 | 132 ± 5 |
| Hematocrit | 40 ± 1 | 40 ± 1 | 39 ± 1 | 42 ± 1 |
| Temperature (°C.) | 37.0 ± 0.1 | 37.0 ± 0.1 | 36.8 ± 0.1 | 36.7 ± 0.1 |
| Post-operative | | | | |
| Weight Change (gm) | −30 ± 8 | −51 ± 5 | −10 ± 6 | −40 ± 5** |
| R Hem. Vol. (mm3) | 696 ± 19 | 689 ± 16 | 711 ± 8 | 716 ± 22 |
| L Hem. Vol. (mm3) | 652 ± 18 | 651 ± 19 | 677 ± 13 | 686 ± 18 |
| Total Vol. (mm3) | 1348 ± 36 | 1340 ± 34 | 1389 ± 19 | 1402 ± 40 |

We claim:

1. A method of preventing the occurrence, or limiting the size, of a region of substantially complete cell death in the brain due to focal ischemic injury, comprising: selecting a mammal that has suffered, or who is at risk of suffering, such a region of substantially complete cell death, and administering bFGF to said mammal intravenously in sufficient dosage to take effect across the blood-brain barrier to effectively prevent the occurrence or limit the size of said region.

2. The method of claim 1, further comprising selecting a mammal that has suffered, or who is at risk of suffering, from constriction or obstruction of a single arterial blood vessel in the brain.

3. The method of claim 1, further comprising selecting a mammal that has suffered, or who is at risk of suffering, from hemorrhage into the brain.

4. The method of claim 3, wherein said hemorrhage is caused by hypertension, hypertensive cerebral vascular disease, trauma, rupture of aneurysms, angiomas, blood dyscrasias, or bleeding from tumors.

* * * * *